United States Patent
Chavan et al.

(10) Patent No.: US 6,486,328 B1
(45) Date of Patent: Nov. 26, 2002

(54) SUBSTITUTED 2-[-6-BENZYL-5-OXO-3-PHENYL-(3S,7S, 7AR)-PERHYDROIMIDAZOL[1,5-C][1,3]THIAZOL-7YL] COMPOUNDS

(75) Inventors: Subhash Prataprao Chavan, Maharashtra (IN); Amar Gopal Chittiboyina, Maharashtra (IN); Subhash Krishnaji Kamat, Maharashtra (IN); Uttam Ramrao Kalkote, Maharashtra (IN); Thotapallil Ravindranathan, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 45 days.

(21) Appl. No.: 09/686,908

(22) Filed: Oct. 12, 2000

(51) Int. Cl.$^7$ .............................................. L07D 513/04
(52) U.S. Cl. .................................... 548/154; 548/303.7
(58) Field of Search ............................... 548/154, 303.7

(56) References Cited

U.S. PATENT DOCUMENTS 5,233,045 A * 8/1993 Schwarz ..................... 548/154
5,274,107 A 12/1993 Ravindranathan et al.

OTHER PUBLICATIONS

A simple and enantioselective synthesis of (+)–Biotin (E.J. Corey and Mukund M. Mehrotra). Tetrahedron Letters, vol. 29. No. 1, pp. 57–60, 1988.
Synthesis of D–Biotin from cysteine (H.L. Lee, E.G. Baggiolini, and M.R. Uskokovic) Tetrahedron vol. 43, No. 21, pp. 4887 to 4903, 1987.
Stereoselektive synthesewege zu (+)–Biotin aus L–Cystein (Eike Poetsch and Michael Casutt) —EP 242, 686, 1986 CA: 108: 112077k 1988; Chimia 41, 148, 1987.
Stereospecific total synthesis of d–Biotin from L(+)–Cysteine (Pat N. Confalone, Giacomo Pizzolato, Enrico G. Baggiolini, Dianne Lollar and Milan R. Uskokovic) —Journal of the American Chemical Society/99:21, Oct. 12, 1977.
Stereospecific synthesis of (+)–Biotin (Hiroshi Ohrui and Sakae Emoto) Tetrahedron Letters No. 32, pp. 2765–2766, 1975.
Stereochemical Control in the addition of Isothiocyanetate Esters to Boron Trifluoride Activated 3–Thiazolines. A Novel Synthesis of d–Biotin. Robert A. Volkmann et al., J. am. chem. Soc. 1983, 105, 5946–5948.
Process for synthesis of D(+) Biotin (Thotapaillil Ravindranathan, Subash P. Chavan, Rajkumar B. Tejwani).
Synthesis of D–(+)–Biotin through Selective Ring Closure of N–Acyliminium Silyl Enol Ethers (Marinus J. Moolenaer, W. Nico Speckamp, Henk Hiemstra, Eike Poetsch, and Michael Casutt) M. Angew. Chem., Int. Ed. Engl. 1995, 34, 2391.
Synthesis of d–Biotin from L–Cystine via Intramolecular [3+2] Cycloaddition —(Enrico G. Baggiolini et al.) J. Am. Chem. Soc. 1982, 104, 6460–6462.

* cited by examiner

*Primary Examiner*—Robert Gerstl
(74) *Attorney, Agent, or Firm*—Smith, Gambrell & Russell, LLP

(57) ABSTRACT

A novel route has been developed for substituted 2-[-6-benzyl-5-oxo-3-phenyl-(3s,7s,7aR)-perhydroimidazol[1,5-c][1,3]thiazol] compounds; crucial intermediates for D(+)-biotin of formula (7) which involves simple, efficient, practical and cost effective protocol. These are crucial intermediates for commercially important D(+)-biotin preparation. These compounds are more stable and are produced by non-hazardous methods.

16 Claims, No Drawings

SUBSTITUTED 2-[-6-BENZYL-5-OXO-3-PHENYL-(3S,7S, 7AR)-PERHYDROIMIDAZOL[1,5-C][1,3]THIAZOL-7YL] COMPOUNDS

FIELD OF THE INVENTION

The invention relates to novel substituted 2-[-6-benzyl-5-oxo-3-phenyl-(3s,7s,7aR)-perhydroimidazol[1,5-c][1,3] thiazol] compounds having general formula (7)

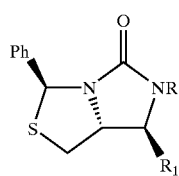

Formula 7

Wherein R=benzyl, R1=alkyl group exemplified by 1-phenyl-1-ethanone, 1-(4-chlorophenyl)-1-ethanone, 1-(4-methoxypheny)-1-ethanone,2-oxocyclohexyl, 1-trimethylsilyloxy-2-oxocyclohexyl, allyl,1-hexanyl,4-dimethylaminophenyl, or 2-methylpropanoate. Still more particularly it relates to methyl 6-[benzyl-5-oxo-3-phenyl-(3S,7aR)-perhydroimidazo[1,5-c][1,3]thiazol-7yl]-6-oxohexanoic acid of formula (1) which is very useful intermediate for D(+)-Biotin

BACKGROUND

Biotin (Vitamin H) is one of the B-complex group of vitamins and has immense commercial importance in the area of animal health and nutrition. It is one of the biocatalysts of the reversible metabolic reactions of carbon dioxide transport in micro and macro organisms. It is used in poultry feeds of rapid growth of chicks and healthy hatching of eggs. Biotin avidin complex finds a vital role in the area of biochemistry. D(+)-Biotin prepared by the process of the present invention is represented by formula 2

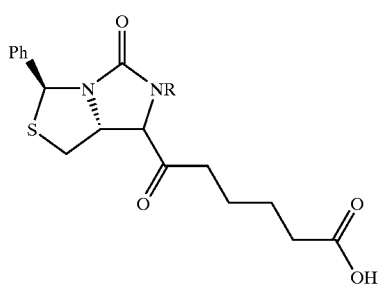

Formula (1)

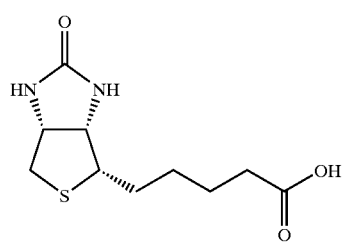

Formula (2)

D(+) Biotin is prepared in the prior art from amino acids viz., cysteine, cyctine and serine. These processes involving L-cystine as the precursor, incorporate intramolecular radical cyclization (E. J. Corey, M. M. Mehrotra, Tet.Lett., 29, 57 1988) as the key step is construct the tetrahydrothiophene moiety of biotin.

Another prior art process involves intramolecular cycloaddition (3+2) of derivatives of L-cystine (E. G. Baggiolini, H. L. Lee, G. Pizzolato and M. R. Uskokovic, J.Am.Chem.Soc., 104, 6460, 1982), and L-cysteine (, H. L. Lee, E. G. Baggiolini and M. R. Uskokovic, Tetrahedron 43, 4887, 1987).

In another process starting from L-cysteine, a bicyclic imidazolidine is the key intermediate leading to D(+)-biotin (E. Poetsch and M. Casutt, EP 242,686 1986 CA:108:1612077k 1988; Chimia 41, 148 1987). In an totally different and novel approach. L-cysteine was converted to its thiazolidine derivative which on treatment with bromine is converted stetreospecifically to a bicyclic intermediate as a single stereoisomer and eventually transformed to D(+)-biotin (P. N. Confalone, E. G. Baggiolini, D. Lollar, and M. R. Uskokovic, J. Am. Chem. Soc., 99, 7020 1977). Process for stereospecific synthesis of D(+)-Biotin from sugars of suitable configuration are known. [From Mannose Tet. Lett., 32, 2765 1975].

The use of L-cysteine in known from U.S. Pat. Nos. 4,000,972, 4,130,713, 4,337,345 and J. Am. Chem. Soc., 99, 7020, 1977 avoids the handling of labile intermediate steps but involves 18 steps, in all with the separation of undesired isomer leading to unsatisfactory yields of optically active D(+)-Biotin.

In another process J. Am. Chem. Soc., 105, 5946, 1983 and EP 0094776, substituted 3H, 5H-Imidazo[1,5-C]tetra hydro thiazole are described from which after racemate resolution, synthesis of optically active biotin is described.

In another process by Moolenaer, M. J.; Speckamp, W. N.; Hiemstra, H.; Poetsch, E.; Casutt, M. Angew. Chem., Int. Ed. Engl. 1995, 34,2391 and DE 3,926,690 involves the intramolecular version of the condensation of a silyl enol ether with N-acyliminium intermediates to effect the ring closure of thio ether to the thiophane nucleus.

In yet another process by Poetsch, E.; Casutt, M., EP 242,686 1986; CA: 108: 112077K 1988; Chimia 41, 141–150, 1987 describes the formation of keto acid and further elaboration of acid to D(+)-Biotin. The main draw back of this method is use of hazardous 2 eq of diisobutylaluminium hydride (DIBAL-H). Potassium cyanide (KCN), Carbonyldiimidazole and involves reactions to be performed under anhydrous conditions.

In yet another prior art of biotin syntheses by Chavan, S. P.; Chittiboyina, A. G.; Kamat, S. K., Indian Patents NF135/98, 136/98 and Ravindranathan, T.; Chavan, S. P.; Tejwani, R. B. U.S. Pat. No. 5,274,107 (1993) describes the formation of substituted imidazolidines from L-cysteine and further elaboration of hydantoin to D(+)-biotin. This process also involves the use of expensive and hazardous chemicals viz., DIBAL-H, tertiary butyl dimethyl silyl chloride (TBDMSCI), trifluoromethane sulphonic acid (Triflic acid) etc., Hitherto known processes involve highly toxic and hazardous chemicals e.g., phosgene for the formation of imidazolidine. Moreover the intramolecular radical cyclization leads to both desired five membered as well as undesired six membered ring along with tin inclusion compounds as the undesired byproducts.

In another prior art process involving the intramolecular (3+2) cylcoaddition reaction of nitrone, the precursor olefin is obtained as a mixture (9:1) of which the desired olefin has to be purified and separated by chromatography. Moreover, the chiral intermediates obtained during the above mentioned sequence of reactions were prone to racemization.

In another prior art process involving the intramolecular cyclization of thiazolidine required Collins oxidation as one of the steps. Use of heavy metals on an industrial scale would lead to problems during waste disposal. Moreover Wittig reaction on the aldehyde leads to a mixture of isomers, which should be separated and the desired isomer subjected to further reactions leading to biotin.

All these processes are however characterized by large number of synthetic steps resulting in low overall yields. The non crystallizable intermediate stages mostly due to sugar nature are often obtained in impure form and require tedious purification on account of their polyfunctionality and chemical liability connected with it maintenance of comparatively very narrow range of reaction parameters. Additionally these sugars are not easily available in nature which leads to high prices.

Hitherto known processes involve highly toxic, expensive and hazardous chemicals for example carbonyldiimidazole, Methyl Iodide, potassium cyanide DIBAL-H etc., for the formation of keto acid (1). More over these reactions required anhydrous conditions.

An object of the present invention is to provide substituted [6-benzyl-5-oxo-3-phenyl-(3S,7S,7aR)-perhydroimidazo[1,5-c][1,3]thiazol]-7yl compounds of formula (7) especially as given table-1 which can be used for synthesis of D(+)-biotin of formula (2).

Another object of the present invention is to provide selective Baeyer Villiger oxidation and new methodology for nucleophilic addition to imidazolodine of the formula (6) at C-7 position for the synthesis of compound having formula (7).

DETAILED DESCRIPTION OF THE INVENTION

Accordingly the present invention provides substituted [6-benzyl-5-oxo-3-phenyl-(3S, 7S, 7aR)-perhydroimidazo [1.5-c][1,3]thiazol]-7yl compounds having general formula (7)

Formula 7

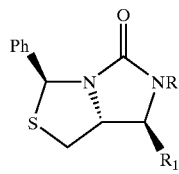

Wherein R=benzyl, $R_1$=alkyl exemplified by 1-phenyl-1-ethanone, 1-(4-chlorophenyl)-1-ethanone, 1-(4methoxypheny)-1-ethanone, 2-oxocyclohexyl, 1-trimethylsilyloxy-2-oxocyclohexyl, allyl, 1-hexynyl, 4-dimethylaminophenyl, or 2-methylpropanoate The present invention also provides a process for the preparation of compounds having formula (7) which comprises reacting the compound of formula (6) with Lewis acid and a nucleophile at a temperature ranging between 0° to 30° C. in an organic solvent for 10–30 minutes quenching the reaction mixture with either water or saturated aqueous solution of quenching agent, separating and concentrating the organic layer, purifying by conventional methods such as chromatography to obtain compounds of formula (7a) to (7g) as mentioned in the following table.

In one of the embodiment of the present invention the compound the alkyl group may be 1-phenyl-1-ethanone, 1-(4-chlorophenyl)-1-ethanone, 1-(4-methoxypheny)-1-ethanone,2-oxocyclohexyl, 1-trimethylsilyloxy-2-oxocyclohexyl, allyl, 1-hexanyl,4-dimethylaminophenyl, or 2-methylpropanoate.

In another embodiment the organic solvent used is selected from the group consisting of dichloromethane, dichloroethane, chloroform, tetrahydrofuran, benzene or toluene.

In still another embodiment the quenching agent is selected from the ammonium chloride, potassium chloride, sodium chloride.

The compound having formula (6) can be prepared by known procedures as per the scheme given herein below:

The present invention also provides a process for the preparation of D(+) biotin of formula (2) as per the scheme given hereinbelow which comprises reacting compound having formula [7(e)/7(e')] with an oxidising agent in presence of alkaline alcohol at temperature ranging between 15–40° C. for the period of 30 mints to 90 min, removing the alcohol by conventional methods and extracting with an organic solvent, separating the aqueous layer and acidifying to pH 4.0 to 5.0 further extracting the mixture with an organic solvent, separating and concentrating the solvent layer, removing the solvent by conventional methods like evaporation to obtain compound of formula (1), converting the compound of formula (1) to obtain D(+) biotin by known methods.

In another embodiments of the present invention the organic solvent used for the reaction may be methanol, ethanol water.

In another embodiment of the present invention the alkali used for the reaction may be KOH, NaOH, $NaHCO_3$, $Na_2CO_3$, $KHCO_3$, $K_2CO_3$.

In still another embodiment the oxidising agent used may be conventional peroxides exemplified by hydrogen peroxide, tertiary butyl hydrogen peroxide and cumene hydroperoxide etc., In a feature of the present invention the electrophile of formula (6) is prepared by known procedure as given in (Poetsch, E.; Casutt, M., EP 242,686 1986; CA: 108: 112077K 1988; Chimia 41, 141–150, 1987).

In another feature the present invention synthesis of D(+)-biotin can be done by obtaining methyl ether of compound having formula (6). The methyl ether can be prepared by conventional methods.

The merits of invented processes are use of easily accessible. cheap chemicals, selective Baeyer-Villiger oxidation and new methodology for the preparation of C-7 substituted imidazolidines, which provides an economically feasible method for the D(+)-biotin synthesis, as the synthesis of biotin of formula (2) from compound of formula (1) is well reported in literature, and avoids the use of costlier and hazardous chemicals such as DIBAL-H, KCN, etc.

EXAMPLES

As aforesaid D(+) biotin can be synthesized using compounds mentioned in table-1. However one will have to follow different approaches for such synthesis.

The process for the preparation of the compounds claimed in the present invention is described herein below which is illustrative only and should not be construed to limit the scope of the present invention in any manner whatsoever.

Example 1

2-[6-Benzyl-5-oxo-3-phenyl-(3S, 7S, 7aR)-perhydroimidazo[1,5-C][1,3]thiazol-7-yl]-1-phenyl-1-ethanone To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1-trimethylsilyloxy styrene (0.384 parts, 2 mmol). Then the solution was cooled to 0° C, and Lewis acid for example borontrifluoride etherate ($BF_3.Et_2O$) (0.142 parts, 1 mmol) was added drop wise. The reaction mixture was stirred at 0° C. for 10 mints, and the reaction mixture was quenched with saturated ammonium chloride (10 parts). Then the organic layer was separated, concentrated and column purification with ethylacetate:pet.ether (15:85) as eluent provided compound 2-[6-benzyl-5-oxo-3-phenyl-(3S, 7S, 7aR)-perhydroimidazo[1,5-C][1,3]thiazol-7-yl]-1-phenyl-1-ethanone of formula (7a) (viscous liquid, 0.419 parts, 0.98 mmol) in 98% yield.

$^1$H NMR ($CDCl_3$) δ: 2.64 (dd, 1H, J=9.3, 10.3 Hz); 3.12 (dd, 1H, J=4.4, 10.3 Hz); 3.34 (m, 2H); 3.77 (m, 1H); 3.80 (m, 1H); 4.16 (d, 1H, J=15.14 Hz); 4.86 (d, 1H, J=15.14, Hz); 6.46 (s, 1H); 7 29 (m, 15H).

Example 2

2-[6-Benzyl-5-oxo-3-phenyl-(3S, 7S, 7aR)-perhydroimidazo[1,5-C][1,3]thiazol-7-yl]-1-(4-chlorophenyl)-1-ethanone To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1-trimethylsilyloxy 4'-chlorostyrene (0.453 parts, 2 mmol). Then the solution was cooled to 0° C., and Lewis acid for example $BF_3.Et_2O$ (0.142 parts, 1 mmol) was added drop wise. The reaction mixture was stirred at 0° C. for 15 mints, and the reaction mixture was quenched with saturated ammonium chloride (10 parts). Then the organic layer was separated, concentrated and column purification with ethylacetate:pet.ether (15:85) as eluent provided compound 2-[6-benzyl-5-oxo-3-phenyl-(3S, 7S, 7aR)-perhydroimidazo[1,5-C][1,3]-thiazol-7-yl]-1-(4-chlorophenyl)-1-ethanone of formula (7b) (viscous liquid, 0.453 parts, 0.98 mmol) in 98% yield.

$^1$H NMR ($CDCl_3$) δ: 2.68 (dd, 1H, J=9.3, 10.3 Hz); 3.09 (dd, 1H, J=9.6, 17.5 Hz); 3.31 (dd, 1H, J=4.6, 10.3 Hz); 3.43 (dd, 1H, J=3.9, 17.5 Hz); 3.75 (dd, 1H, J=6.3, 9.1 Hz); 3.92 (dd, 1H, J=3.9, 9.3 Hz); 4.16 (d, 1H, J=15.14 Hz); 4.81 (d, 1H, J=15.14 Hz); 6.45 (s, 1H) 7.28 (m, 10H); 7.39 (d, 2H, J=8.79 Hz), 7.76 (d, 2H, J=8.79 Hz).

Example 3

2-[6-Benzyl-5-oxo-3-phenyl-(3S, 7S, 7aR)-perhydroimidazo[1,5-C][1,3]thiazol-7-yl]-1-(4-methoxyphenyl)-1-ethanone To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1-trimethylsilyloxy 4'-methoxystyrene (0.444 parts, 2 mmol). Then the solution was cooled to 10° C. and Lewis acid for example $BF_3.Et_2O$ (0.142 parts, 1 mmol) was added drop wise. The reaction mixture was stirred at 10° C. for 20 mints, and the reaction mixture was quenched with saturated ammonium chloride (10 parts). Then the organic layer was separated, concentrated and column purification with ethylacetate:pet.ether (15:85) as eluent provided compound 2-[6-benzyl-5-oxo-3-phenyl-(3S, 7S, 7aR)-perhydroimidazo[1,5-C][1,3]-thiazol-7-yl]-1-(4-methoxyphenyl)-1-ethanone of formula (7c) (viscous liquid, 0.449 parts, 0.98 mmol) in 98% yield.

$^1$H NMR ($CDCl_3$) δ: 2.67 (dd, 1H, J=8.7, 10.3 Hz); 3.15 (dd, 1H, J=9.4, 17.4 Hz); 3.34 (m, 2H); 3.77 (m, 3H); 3.88 (s, 1H); 4.16 (d, 1H, J=15.14 Hz); 4.86 (d, 1H, J=15.14 Hz); 6.46 (s, 1H); 6.93 (d, 2H, J=8.79); 7.31 (m, 10H); 7.83 (d, 2H, J=8.79 Hz).

Example 4

6-Benzyl-7-(2-oxocyclohexyl)-3-phenyl-(3S, 7S, 7aR)-perhydroimidazo[1,5-C][1,3]thiazol-5-one To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1-trimethylsilyloxy-1-cyclohexene (0.340 parts. 2 mmol). Then the solution was cooled to 20° C., and Lewis acid for example $BF_3.Et_2O$ (0.142 parts, 1 mmol) was added drop wise. The reaction mixture was stirred at 20° C. for 10 mints. and the reaction mixture was quenched with saturated ammonium chloride (10 parts). Then the organic layer was separated, concentrated and column purification with ethylacetate:pet.ether (15:85) as eluent provided compound 6-benzyl-7-(2-oxocyclohexyl)-3-phenyl-(3S, 7S, 7aR)-perhydroimidazo[1,5-C][1,3]-thiazol-5-one of formula (7d) (viscous liquid, 0.398 parts, 0.98 mmol) in98% yield.

$^1$H NMR ($CDCl_3$) δ: 1.65 (m, 2H); 1.9–2.1 (m, 4H); 2.32 (t, 2H); 2.56 (ddd, 1H, J=4.5, 6.7, 11.2 Hz); 3.33 (dd, 1H, J=6, 10 Hz); 3.64 (ddd, 1H, J=6.1, 7.6, 9 Hz); 3.87 (ddd, 1H, J=2, 4.7, 12.3 Hz); 4.12 (d, 1H, J=15.12 Hz); 4.70 (d, 1H, J=15.12 Hz); 6.37 (s, 1H); 7.38 (m, 10H).

Example 5

6-Benzyl-7-(1-trimethylsilyloxy-2-oxocyclohexyl)-3-phenyl-(3S, 7R, 7aR)-perhydroimidazo[1,5-C][1,3]thiazole-5-one To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1,2-bistrimethylsilyloxy cyclohexene (0.516 parts, 2 mmol). Then the solution was cooled to 0° C. and Lewis acid for example $BF_3.Et_2O$ (0.142 parts, 1 mmol) was added drop wise. The reaction mixture was stirred at 0° C. for 10 mints. and the reaction mixture was quenched with saturated ammonium chloride (10 parts). Then the organic layer was separated, concentrated and column purification with ethylacetate:pet.ether (15:85) as eluent provided compound 6-benzyl-7-(1-trimethylsilyloxy-2-oxocyclohexyl)-3-phenyl-(3S, 7R, 7aR)-perhydroimidazo[1,5-C][1,3]thiazole-5-one of formula (7e) (viscous liquid, 0.376 parts, 0.76 mmol) in 76% yield. And with ethyl acetate:pet.ether (25:75) as eluent provided the compound 6-benzyl-7-(1-hydroxy-2-oxocyclohexyi)-3-phenyl-(3S, 7R, 7aR)-perhydroimidazo[1,5-C][1,3]thiazole-5-one of formula (7e') (highly viscous liquid, 0.093 parts. 0.22 mmol) in 22% yield.

$^1$H NMR ($CDCl_3$) δ: 0.05 (s, 6H); 0.12 (s, 6H); 1.6–2.1 (m, 6H); 2.15–2.3 (m, 2H); 2.59 (m, 1H); 3.01(dd, 1H, J=6.1, 10.3 Hz); 3.89 (m, 2H); 4.13 (d, 1H, J=15.14 Hz); 4.81 (d, 1H, J=15.14 Hz); 6.48 (s, 1H); 7.38 (m, 10H).

Example 6

6-Benzyl-7-(1-trimethylsilyloxy-2-oxocyclohexyl)-3-phenyl-(3S, 7R, 7aR)-perhydroimidazo[1,5-C][1,3]thiazole-5-one To a solution of compound 6-benzyl-7-hydroxy-3-phenyl-(3S, 7aR)-perhydroimidazo[1,5-C][1,3]thiazol-5-one of formula (6) (0.340 parts, 1 mmol) in dichloromethane (10 parts) was added 1,2-bistrimethylsilyloxy cyclohexene (0.516 parts, 2 mmol). Then the solution was cooled to 10° C., and Lewis acid for example $BF_3.Et_2O$ (0.142 parts, 1 mmol) was added drop wise. The reaction mixture was stirred at 10° C. for 10 mints, and the reaction mixture was quenched with saturated ammonium chloride (10 parts). Then the organic layer was separated, concentrated and column purification with ethylacetate:pet.ether (15:85) as eluent provided compound 6-benzyl-7-(1-trimethylsilyloxy-2-oxocyclohexyl)-3-phenyl-(3S, 7R, 7aR)-perhydroimidazo[1,5-C][1,3]thiazole-5-one of formula (7e) (viscous liquid, 0.490 parts, 0.98 mmol) in 98% yield.

Example 7

7-Allyl-6-benzyl-3-phenyl-(3S, 7S, 7aR)-perhydroimidazo[1,5-C][1,3]thiazol-5-one To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added allyltrimethylsilane (0.228 parts, 2 mmol). Then Lewis acid for example $BF_3.Et_2O$ (0.142 parts, 1 mmol) was added drop wise to reaction mixture at 30° C. was stirred for 30 mints. and the reaction mixture was quenched with saturated ammonium chloride (10 parts). Then the organic layer was separated, concentrated and column purification with ethylacetate:pet.ether (15:85) as eluent provided compound 7-allyl-6-benzyl-3-phenyl-(3S, 7S, 7aR)-perhydroimidazo[1,5-C][1,3]thiazol-5-one of formula (7f) (viscous liquid, 0.343 parts, 0.98 mmol) in 98% yield.

$^1$H NMR (CDCl$_3$) δ: 2.4 (m, 2H); 2.55 (dd, 1H, J=9, 10 Hz); 3.07(dd, 1H, J=6, 10 Hz); 3.35 (m, 1H); 3.80 (m, 1H); 4.08 (d, 1H, J=15.14 Hz); 4.96 (d, 1H. J=15.14 Hz), 5.18 (m, 2H); 5.76 (m, 1H); 6.46 (s, 1H); 7.32 (m, 10H).

Example 8

6-Benzyl-7-(1-hexynyl)-3-phenyl-(3S, 7S, 7aR)-perhydroimidazo[1,5-c][1,3]thiazol-5-one To a solution of compound 6-benzyl-7-hydroxy-3-phenyl-(3S, 7aR)-perhydroimidazo[1,5-C][1,3]thiazol-5-one of formula (6) (0.326 parts, 1 mmol) in dichloromethane (10 parts) was added 1-(tri n-butyltin)hexyne(0.742 parts, 2 mmol). Then the solution was cooled to 0° C., and Lewis acid for example $BF_3.Et_2O$ (0.142 parts, 1 mmol) was added drop wise. The reaction mixture was stirred at 0° C. for 10 mints, and the reaction mixture was quenched with saturated ammonium chloride (10 parts). Then the organic layer was separated, concentrated and column purification with ethylacetate:pet.ether (15:85) as eluent provided compound 6-benzyl-7-(1-hexynyl)-3-phenyl-(3S, 7S, 7aR)-perhydroimidazo[1,5-c][1.3]thiazol-5-one of formula (7g) (viscous liquid, 0.382 parts, 0.98 mmol) in 98% yield.

$^1$H NMR (CDCl$_3$) δ: 0.98 (t, 3H); 1.50 (m, 4H); 2.27 (t, 2H); 2.62 (dd, 1H, J=10.3 Hz); 3.12 (dd, 1H, J=6.3. 10.4 Hz); 3.96 (d, 1H, J=1.5 Hz); 4.06 (dd 1H, 6.3, 9.0 Hz); 4.1 (d, 1H, J=14.7 Hz); 5.0 (d, 1H, J=14.7 Hz); 6.46 (s, 1H); 7.32 (m, 10H).

Example 9

Methyl 6-[6-benzyl-5-oxo-3-phenyl-(3S, 7aR)-perhydroimidazo[1,5-c][1,3]thiazol-7yl]-6-oxohexanoic acid To an alkaline solution of methanol (0.168 parts, 3 mmol of KOH was dissolved in 10 parts of methanol) was added compound of formula (7e) (0.494 parts. 1 mmol). The solution was cooled to 0° C. and then t-butylhydrogen peroxide (0.180 parts, 2 mmol) was added in drop wise. The reaction mixture was stirred for an additional 30 mints. After 30 mints the methanol was removed and extracted with ethylacetate. The aqueous layer was acidified to ~pH 3–4 and extracted with ethylacetate. Evaporation under reduced pressure furnished the compound process for 6-[6-benzyl-5-oxo-3-phenyl-(3S, 7aR)-perhydroimidazo[1,5-c][1,3]thiazol-7yl]-6-oxohexanoic acid of formula (1) (0.326 parts, 0.75 mmol) in 75% yield. This acid was characterized by its derivative as a methyl ester.

$^1$H NMR (CDCl$_3$) δ: 1.55 (m, 4H); 2.27 (m, 2H); 2.44 (m, 2H); 2.58 (dd, 1H, J=9.3, 10.3 Hz); 3.17 (dd, 1H, J=6.3, 10.3 Hz); 3.66 (s, 3H); 3.75 (s, 1H); 3.80 (dd, 1H, J=6.3, 9.0 Hz); 4.06 (d, 1H, J=14.65 Hz); 4.98 (d, 1H, J=14.65 Hz); 6.45 (s, 1H); 7.36 (m, 10H).

Example 10

Methyl 6-[6benzyl-5-oxo-3-phenyl-(3S, 7aR)-perhydroimidazo[1,5-c][1,3]thiazol-7yl]-6oxohexanoic acid To an alkaline solution of methanol (0.168 parts, 3 mmol of KOH was dissolved in 10 parts of methanol) was added compound of formula (7e') (0.422 parts, 1 mmol). The solution was cooled to 0° C. and then t-butylhydrogen peroxide (0.180 parts, 2 mmol) was added in drop wise. The reaction mixture was stirred for an additional 30 mints. After 30 mints the methanol was removed and extracted with ethylacetate. The aqueous layer was acidified to ~pH 3–4 and extracted with ethylacetate. Evaporation under reduced pressure furnished the compound process for 6-[6-benzyl-5-oxo-3-phenyl-(3S, 7aR)-perhydroimidazo[1,5-c][1,3]thiazol-7yl]-6-oxohexanoic acid of formula (1) (0.326 parts, 0.75 mmol) in 75% yield. This acid was characterized by its derivative as a methyl ester as mentioned in example 11.

Example 11

Methyl 6-[6-benzyl-5-oxo-3-phenyl-(3S, 7aR)-perhydroimidazo[1,5-c][1,3]thiazol-7yl]-6-oxohexanoic acid To an alkaline solution of methanol (0.168 parts, 3 mmol of KOH was dissolved in 10 parts of methanol) was added compound of formula (7e) (0.494 parts, 1 mmol). The solution was cooled to 0° C. and then hydrogen peroxide (0.128 parts, 4 mmol) was added in drop wise. The reaction mixture was stirred for an additional 30 mints. After 30 mints the methanol was removed and extracted with ethylacetate. The aqueous layer was acidified to ~pH 3–4 and extracted with ethylacetate. Evaporation under reduced pressure furnished the compound process for 6-[6-benzyl-5-oxo-3-phenyl-(3S, 7aR)-perhydroimidazo[1,5-c][1,3]thiazol-7yl]-6-oxohexanoic acid of formula (1) (0.196 parts, 0.45 mmol) in 45% yield. This acid was characterized by its derivative as a methyl ester as mentioned in example 11.

Example 12

Methyl 6-[6-benzyl-5-oxo-3-phenyl-(3S, 7aR)-perhydroimidazo[1,5-c][1,3]thiazol-7yl]-6-oxohexanoic acid To an alkaline solution of methanol (0.168 parts, 3 mmol of KOH was dissolved in 10 parts of methanol) was added compound of formula (7e) (0.494 parts, 1 mmol). The solution was cooled to 0° C. and then cumenehydroperoxide (0.240 parts, 2 mmol) was added in drop wise. The reaction mixture was stirred for an additional 30 mints. After 30 mints the methanol was removed and extracted with ethylacetate. The aqueous layer was acidified to ~pH 3–4 and extracted with ethylacetate. Evaporation under reduced pressure furnished the compound process for 6-[6-benzyl-5-oxo-3-phenyl-(3S, 7aR)-perhydroimidazo[1,5-c][1,3]thiazol-7yl]-6-oxohexanoic acid of formula (1) (0.260 parts, 0.60 mmol) in 60% yield. This acid was characterized by its derivative as a methyl ester as mentioned in example 11.

The main advantages of the present invention are:
1. Novelty
2. Simplicity
3. Ease of Operation
4. Short Reaction Time
5. Non-anhydrous conditions.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. A substituted 2-[-6-benzyl-5-oxo-3-phenyl-(3s,7s, 7aR)-perhydroimidazol[1,5-c][1,3]thiazol] of formula (7):

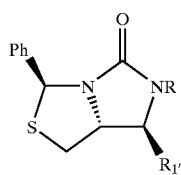

Formula 7' wherein R=benzyl, and $R_1$=a member selected from the group consisting of 1-phenyl-1-ethanone, 1-(4-chlorophenyl)-1-ethanone, 1-(4-methoxypheny)-1-ethanone, 2-oxocyclohexyl, 1-trimethylsilyloxy-2-oxocyclohexyl, allyl, 1-hexanyl, 4-dimethylaminophenyl, and 2-methylpropanoate.

2. The substituted 2-[-6-benzyl-5-oxo-3-phenyl-(3s,7s, 7aR)-perhydroimidazol[1,5-c][1,3 ]thiazol] as claimed in claim 1, selected from the group consisting of:

7a) 2-[6-benzyl-5-oxo-3-phenyl-(3S,7S,7aR)-perhydroimidazo[1,5-c][1,3]thiazol-7-yl]-1-phenyl ethanone,
7b) 2-[6-benzyl-5-oxo-3-phenyl-(3S,7S,7aR)-perhydroimidazo[1,5-c][1,3]thiazol-7-yl]-1-(4-chlorophenyl)-1-ethanone,
7c) 2-[6-benzyl-5-oxo-3-phenyl-(3S,7S,7aR)-perhydroimidazo[1,5-c][1,3]thiazol-7-yl]-1-(4-methoxyphenyl)-1-ethanone,
7d) 6 benzyl-7-(2-oxocyclohexyl)-3-phenyl-(3S,7S,7ar)-perhydroimidazol[1,5-c][1,3]thiazol-5-one,
7e) 6 benzyl -7-(1-trimethylsilyloxy-2-oxocyclohexyl)-3-phenyl-(3S,7S,7ar)-perhydroimidazol[1,5-c][1,3]thiazol-5-one,
7e') 6 benzyl-7-(1-hydroxy-2-oxocyclohexyl)-3-phenyl-(3S, 7S,7ar)-perhydroimidazol[1,5-c][1,3]thiazol-5-one,
7f) 7-allyl-6-benzyl-3-phenyl-(3S,7S,7ar)-perhydroimidazol[1,5-c][1,3]thiazol-5-one, and
7d) 6 benzyl-7-(1-hexynyl)-3-phenyl-(3S,7S,7ar)-perhydroimidazol[1,5-c][1,3]thiazol-5-one.

3. A process for the preparation of compounds having formula 7

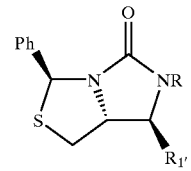

Formula 7' wherein R=benzyl, and $R_1$=a member selected from the group consisting of 1-phenyl-1-ethanone, 1-(4-chlorophenyl)-1-ethanone, 1-(4-methoxypheny)-1-ethanone, 2-oxocyclohexyl, 1-trimethylsilyloxy-2-oxocyclohexyl, allyl, 1-hexanyl, 4-dimethylaminophenyl, and 2-methylpropanoate, said process comprising:

a) reacting compound of formula 6
   with Lewis acid and a nucleophilic agent at a temperature ranging between 0° to 30° C. in an organic solvent for 10–30 minutes,
b) quenching the reaction mixture with either water or saturated alkaline aqueous solution as quenching agent,
c) separating and concentrating the organic layer,
d) purifying to obtain compound of formula (7).

4. A process as claimed in claim 3 wherein the organic solvent used is selected from the group consisting of dichloromethane, dichloroethane, chloroform, tetrahydrofuran, benzene and toluene.

5. A process as claimed in claim 3, wherein the quenching agent is selected from the ammonium chloride, potassium chloride, and sodium chloride.

6. A process for the preparation of keto acid formula (1): said process comprising:

a) reacting a compound having formula 7e) 6 benzyl-7-(1-trimethylsilyloxy-2-oxocyclohexyl)-3-phenyl-(3S, 7S, 7aR)-perhydroimidazo[1,5-c][1,3]thiazol-5-one, or
7e') 6 benzyl-7-(1-hydroxy-2-oxocyclohexyl)-3-phenyl-(3S, 7S, 7aR)-perhydroimidazo[1,5-c][1,3]thiazol-5-one, with an oxidizing agent in presence of alkaline alcohol at temperature ranging between 15–40° C. for the period of 30–90 min,
b) removing the alcohol and extracting with an organic solvent,
c) separating the aqueous layer and acidifying to pH 4.0 to 5.0,
d) further extracting the mixture with an organic solvent,
e) separating and concentrating the solvent layer,
f) removing the solvent to obtain compound of formula (1), and optionally,
g) converting the compound of formula (1) to obtain D(+) biotin.

7. A process as claimed in claim 6, wherein the organic solvent is selected from water, ethanol, and methanol.

8. A process as claimed in claim 6, wherein the alkali used in the reaction is selected from the group consisting of KOH, NaOH, $NaHCO_3$, $Na_2CO_3$, $KHCO_3$, and $K_2CO_3$.

9. A process as claimed in claim 6, wherein, the oxidizing agents used are conventional peroxides selected from hydrogen peroxide, tertiary butyl hydrogen peroxide and cumene hydro peroxide.

10. A process as claimed in claim 6, wherein, the organic layer is separated, concentrated and column purified with ethylacetate: petroleum either (15:85) as eluent.

11. A process as claimed in claim 3, wherein purification is by chromatography.

12. A process as claimed in claim 6, wherein the solvent is removed by evaporation.

13. A process as claimed in claim 3, wherein the nucleophilic agent is selected from the group consisting of 1-trimethyl silyoxy styrene, 1-trimethyl siloxy-4-chlorostyrene, 1-trimethyl silyoxy-4'-methoxy styrene, 1-trimethylsiloxy-1-cyclohexane, 1,2-bistrimethyl silyoxy cyclohexane, 1-(tri-n-butyltin)hexyne, and allyltrimethylsilane.

14. A process as claimed in claim 6, wherein the organic solvent used in step d) is selected from the group consisting of dichloromethane, carbon tetrachloride, chloroform, and ethyl acetate.

15. A process as claimed in claim 14, wherein the organic solvent is ethyl acetate.

16. process as claimed in claim 6, wherein concentration is performed by removing the solvent under pressure.

* * * * *